(12) United States Patent
Chen et al.

(10) Patent No.: US 9,061,955 B2
(45) Date of Patent: Jun. 23, 2015

(54) METHOD OF CONVERTING A COAL TO CHEMICALS

(71) Applicant: UOP LLC, Des Plaines, IL (US)

(72) Inventors: John Q. Chen, Glenview, IL (US); Peter K. Coughlin, Mundelein, IL (US); Stanley J. Frey, Palatine, IL (US); James A. Johnson, Burr Ridge, IL (US); Vasant P. Thakkar, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/468,757

(22) Filed: Aug. 26, 2014

(65) Prior Publication Data

US 2015/0137043 A1   May 21, 2015

Related U.S. Application Data

(60) Provisional application No. 61/905,934, filed on Nov. 19, 2013.

(51) Int. Cl.

| | |
|---|---|
| C07C 2/06 | (2006.01) |
| C07C 2/76 | (2006.01) |
| C10G 65/10 | (2006.01) |
| C07C 2/42 | (2006.01) |
| C07C 2/08 | (2006.01) |
| C07C 4/04 | (2006.01) |
| C07C 4/06 | (2006.01) |
| C07C 7/12 | (2006.01) |
| C07C 5/333 | (2006.01) |
| C01B 3/02 | (2006.01) |

(52) U.S. Cl.
CPC ... *C07C 2/42* (2013.01); *C07C 2/08* (2013.01); *C07C 4/04* (2013.01); *C07C 4/06* (2013.01); *C07C 7/12* (2013.01); *C07C 5/333* (2013.01); *C01B 3/02* (2013.01); *C07C 2529/89* (2013.01); *C07C 2523/62* (2013.01)

(58) Field of Classification Search
USPC ............. 585/322, 319, 407, 518; 208/58, 60, 208/108, 125

See application file for complete search history.

(56) References Cited

U.S. PATENT DOCUMENTS

| | | | |
|---|---|---|---|
| 3,623,973 A * | 11/1971 | Tarhan | ........................ 208/60 |
| 5,437,782 A | 8/1995 | Kerby et al. | |
| 2013/0178673 A1 | 7/2013 | Kim et al. | |

FOREIGN PATENT DOCUMENTS

| | | |
|---|---|---|
| CN | 101274874 | 10/2008 |
| EP | 2630106 | 4/2012 |
| GB | 540022 | 10/1941 |

OTHER PUBLICATIONS

Cypres, R., "Aromatic hydrocarbons formation during coal pyrolysis," Fuel Processing Technology (1987), 15th, 1-15.

* cited by examiner

*Primary Examiner* — Thuan D Dang

(57) ABSTRACT

A method of processing a coal feed to produce aromatic hydrocarbon compounds includes providing a coal tar stream and converting the coal tar stream to a conversion product comprising at least olefins, paraffins, and aromatics. The process further includes separating the olefins and $C_5^-$ paraffins from the conversion product, and contacting the separated olefins and the $C_5^-$ paraffins with a catalyst to dehydrogenize, oligomerize, and cyclize the olefins and the $C_5^-$ paraffins, to form aromatic hydrocarbon compounds.

7 Claims, 2 Drawing Sheets

METHOD OF CONVERTING A COAL TO CHEMICALS

RELATED APPLICATIONS

This application claims priority to U.S. Provisional Application No. 61/905,934 filed on Nov. 19, 2013, the entirety of which is incorporated herein.

BACKGROUND OF THE INVENTION

Many different types of chemicals are produced from the processing of petroleum. However, petroleum is becoming more expensive because of increased demand in recent decades.

Therefore, attempts have been made to provide alternative sources for the starting materials for manufacturing chemicals. Attention is now being focused on producing liquid hydrocarbons from solid carbonaceous materials, such as coal, which is available in large quantities in countries such as the United States and China.

Pyrolysis of coal produces coke and coal tar. The coke-making or "coking" process consists of heating the material in closed vessels in the absence of oxygen to very high temperatures. Coke is a porous but hard residue that is mostly carbon and inorganic ash, which may be used in making steel.

Coal tar is the volatile material that is driven off during heating, and it comprises a mixture of a number of hydrocarbon compounds. It can be separated to yield a variety of organic compounds, such as benzene, toluene, xylene, naphthalene, anthracene, and phenanthrene. These organic compounds can be used to make numerous products, for example, dyes, drugs, explosives, flavorings, perfumes, preservatives, synthetic resins, and paints and stains. The residual pitch left from the separation is used for paving, roofing, waterproofing, and insulation.

Coal tar can be used to produce desirable and valuable products such as olefins and aromatic compounds including benzene, toluene, and xylenes. Thus, there is a need for a process for converting coal tar to one or more of olefins and aromatic compounds.

SUMMARY OF THE INVENTION

In a first aspect, a method of processing a coal feed to produce aromatic hydrocarbon compounds includes providing a coal tar stream, and converting the coal tar stream to a conversion product comprising at least olefins, paraffins, and aromatics. The process further includes separating the olefins and $C_5^-$ paraffins from the conversion product, and contacting the separated olefins and the $C_5^-$ paraffins with a catalyst to dehydrogenize, oligomerize, and cyclize the olefins and the $C_5^-$ paraffins, to form aromatic hydrocarbon compounds.

In another aspect, a method of processing a coal tar feed stock to increase olefin production includes converting the coal tar feed stock to a conversion product comprising olefins, paraffins, and aromatics. The conversion product is separated to produce at least an olefin stream, a light paraffin stream, and an aromatics stream. The light paraffin stream is then dehydrogenated to produce additional olefins.

DETAILED DESCRIPTION OF THE INVENTION

Figure 1:
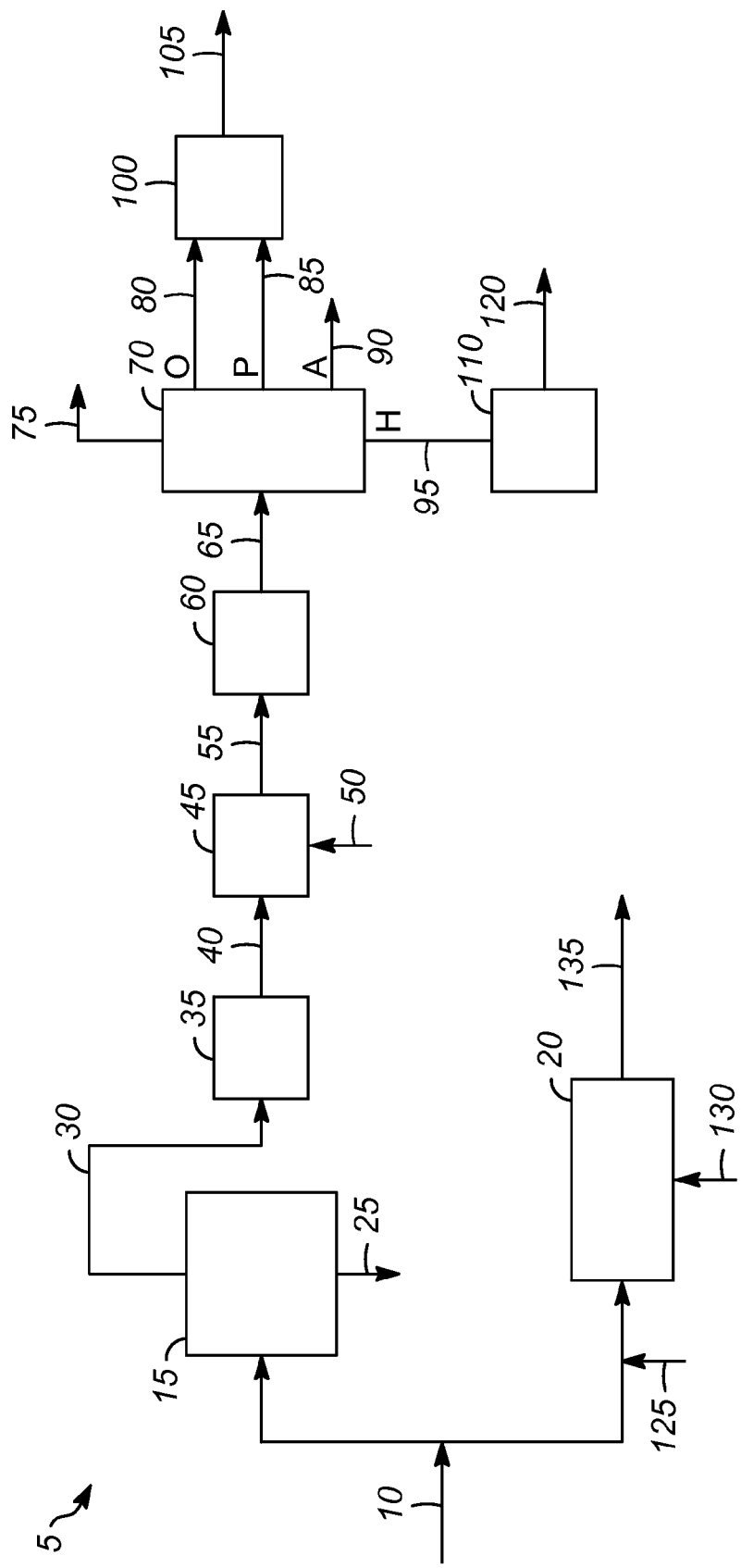
FIG. 1 illustrates one embodiment of the process of the present invention.

FIG. 1 shows one embodiment of a coal conversion process 5. A coal feed 10 can be sent to a pyrolysis zone 15 such as a coking oven, a gasification zone 20, or the coal feed 10 can be split into two parts and sent to both.

In the pyrolysis zone 15, the coal is heated at high temperature, e.g., up to about 2,000° C. (3,600° F.), in the absence of oxygen to drive off the volatile components. Coking produces a coke stream 25 and coal tar stream 30. The coke stream 25 can be used in other processes, such as the manufacture of steel.

The coal tar stream 30 which comprises the volatile components from the coking process can be sent to a contamination removal zone 35, if desired.

The optional contaminant removal zone 35 for removing one or more contaminants from the coal tar stream or another process stream may be located at various positions along the process depending on the impact of the particular contaminant on the product or process and the reason for the contaminant's removal, as described further below. For example, the contaminant removal zone 35 can be positioned upstream of a separation zone 70. Some contaminants have been identified to interfere with a downstream processing step or hydrocarbon conversion process, in which case the contaminant removal zone 35 may be positioned upstream of the separation zone 70 or between the separation zone 70 and the particular downstream processing step at issue. Still other contaminants have been identified that should be removed to meet particular product specifications. Where it is desired to remove multiple contaminants from the hydrocarbon or process stream, various contaminant removal zones 35 may be positioned at different locations along the process. In still other approaches, a contaminant removal zone 35 may overlap or be integrated with another process within the system, in which case the contaminant may be removed during another portion of the process, including, but not limited to the separation zone 70 or the downstream hydrocarbon conversion zone. This may be accomplished with or without modification to these particular zones, reactors or processes. While the contaminant removal zone 35 is often positioned downstream of the hydrocarbon conversion reactor, it should be understood that the contaminant removal zone 35 in accordance herewith may be positioned upstream of the separation zone 70, between the separation zone 70 and the hydrocarbon conversion zone, or downstream of the hydrocarbon conversion zone or along other streams within the process stream, such as, for example, a carrier fluid stream, a fuel stream, an oxygen source stream, or any streams used in the systems and the processes described herein. The contaminant concentration is controlled by removing at least a portion of the contaminant from the coal tar stream 30. As used herein, the term removing may refer to actual removal, for example by adsorption, absorption, or membrane separation, or it may refer to conversion of the contaminant to a more tolerable compound, or both.

The decontaminated coal tar feed 40 is sent to a hydrotreating zone 45. Hydrotreating is a process in which hydrogen gas 50 is contacted with a hydrocarbon stream in the presence of suitable catalysts which are primarily active for the removal of heteroatoms, such as sulfur, nitrogen, oxygen, and metals from the hydrocarbon feedstock. In hydrotreating, hydrocarbons with double and triple bonds may be saturated. Aromatics may also be saturated. Typical hydrotreating reaction conditions include a temperature of about 290° C. (550° F.) to about 455° C. (850° F.), a pressure of about 3.4 MPa (500 psig) to about 27.6 MPa (4,000 psig), a liquid hourly space velocity of about 0.1 hr$^{-1}$ to about 4 hr$^{-1}$, and a hydrogen rate of about 168 to about 1,685 Nm$^3$/m$^3$ oil (1,000-10,000 scf/bbl). Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum.

A hydrotreated stream 55 is then routed from the hydrotreating zone 45 to a conversion zone 60. The conversion zone 60 converts the hydrotreated coal tar stream 55 to a conversion product 65 comprising at least olefins, paraffins, and aromatic hydrocarbons. Conversion can take the form of, for example, a thermal cracking process or a fluid catalytic cracking process.

Thermal cracking heats the provided hydrocarbon stream to a temperature in the range of about 550° C. to about 900° C., at an absolute pressure of about 7,000 kPa. The high temperature and pressure causes disproportionation, where "light" (i.e. lower molecular weight), hydrogen-rich products are formed at the expense of heavier molecules which condense and are depleted of hydrogen.

Fluid catalytic cracking (FCC) is a catalytic hydrocarbon conversion process accomplished by contacting heavier hydrocarbons in a fluidized reaction zone with a catalytic particulate material. The reaction in catalytic cracking is carried out in the absence of substantial added hydrogen or the consumption of hydrogen. The process typically employs a powdered catalyst having the particles suspended in a rising flow of feed hydrocarbons to form a fluidized bed. In representative processes, cracking takes place in a riser, which is a vertical or upward sloped pipe. Typically, a pre-heated feed is sprayed into the base of the riser via feed nozzles where it contacts hot fluidized catalyst and is vaporized on contact with the catalyst, and the cracking occurs converting the high molecular weight oil into lighter components including liquefied petroleum gas (LPG), gasoline, and a distillate. The catalyst-feed mixture flows upward through the riser for a short period (a few seconds), and then the mixture is separated in cyclones. The hydrocarbons are directed to a fractionator for separation into LPG, gasoline, diesel, kerosene, jet fuel, and other possible fractions. While going through the riser, the cracking catalyst is deactivated because the process is accompanied by formation of coke which deposits on the catalyst particles. Contaminated catalyst is separated from the cracked hydrocarbon vapors and is further treated with steam to remove hydrocarbon remaining in the pores of the catalyst. The catalyst is then directed into a regenerator where the coke is burned off the surface of the catalyst particles, thus restoring the catalyst's activity and providing the necessary heat for the next reaction cycle. The process of cracking is endothermic. The regenerated catalyst is then used in the new cycle. Typical FCC conditions include a temperature of about 400° C. to about 800° C., a pressure of about 0 to about 688 kPag (about 0 to 100 psig), and contact times of about 0.1 seconds to about 1 hour. The conditions are determined based on the hydrocarbon feedstock being cracked, and the cracked products desired. Zeolite-based catalysts are commonly used in FCC reactors, as are composite catalysts which contain zeolites, silica-aluminas, alumina, and other binders.

Following the conversion process, the conversion product 65 is routed to the separation zone 70, where it is separated into two or more fractions 75, 80, 85, 90, 95. As discussed above, the conversion product 65 includes a mixture of hydrocarbon materials, comprising at least olefins, paraffins, and aromatic hydrocarbons, each with a range of initial boiling points.

As illustrated, the conversion product 65 is separated into a gas fraction 75 containing gases such as NH$_3$ and CO as well as light hydrocarbons, such as ethane, an olefin fraction 80, a paraffin fraction 85, an aromatics fraction 90, and a heavy non-aromatic hydrocarbon fraction 95.

Suitable separation processes include, but are not limited to fractionation, solvent extraction, and distillation.

One or more of the fractions 75, 80, 85, 90, 95 can be further processed, as desired. As illustrated in FIG. 1, the olefin stream 80 and the paraffin stream 85 including at least paraffins having five or fewer carbon atoms are routed to a dehydrogenizing, oligomerizing, and cyclizing zone 100. The olefins and paraffins in the olefin stream 80 and the paraffin stream 85 are contacted with a conversion catalyst to produce an aromatic hydrocarbons stream 105. The catalyst preferably includes an acid function, a metal function, or both acid and metal functions. One particular example of such a catalyst is a catalytic composite comprising a gallium component and a crystalline aluminosilicate incorporated with a phosphorus containing alumina.

Returning to the separation zone 70, additionally, the heavy non-aromatic hydrocarbon fraction 95 is further processed. The heavy non-aromatic hydrocarbon fraction 95 includes relative high molecular weight non-aromatic hydrocarbons. In particular, the heavy non-aromatic hydrocarbon fraction 95 can include non-aromatic hydrocarbons including six or more carbon atoms. The heavy non-aromatic hydrocarbon fraction 95 is routed to a catalytic reforming zone 110. In the reforming zone 110, the heavy non-aromatic hydrocarbon fraction 95 is contacted with a platinum-containing catalytic reforming catalyst. Examples of such a catalyst include a reforming catalyst can include indium, tin, and a catalytically effective amount of a Group VIII element for one or more reforming reactions. Alternatively, an example catalyst may contain multiple Group VIII (8-10) noble metals having different gradients within the catalyst and a nonacidic large-pore molecular sieve. Still other example catalysts include a refractory inorganic oxide and halogen, platinum-group metal, and Group IVA (14) metal components, wherein the Group IVA (14) metal is homogeneously dispersed within a bed of catalyst particles. Contacting the heavy non-aromatic hydrocarbon fraction 95 with the catalytic reforming catalyst produces a reformed aromatics stream 120 including aromatic hydrocarbons, such as benzene, toluene, and xylenes.

Additionally, one or more of the streams 75, 90, 95 from the separation zone 70, as well as the aromatic hydrocarbons stream 105 and the reformed aromatics stream 120 can be sent to additional downstream conversion zones including, but are not limited to, transalkylation zones, alkylation zones, oxidation zones, and hydrogenation zones.

Transalkylation is a chemical reaction resulting in transfer of an alkyl group from one organic compound to another. Catalysts, particularly zeolite catalysts, are often used to effect the reaction. If desired, the transalkylation catalyst may be metal stabilized using a noble metal or base metal, and may contain suitable binder or matrix material such as inorganic oxides and other suitable materials. In a transalkylation process, a polyalkylaromatic hydrocarbon feed and an aromatic hydrocarbon feed are provided to a transalkylation reaction zone. The feed is usually heated to reaction temperature and then passed through a reaction zone, which may comprise one or more individual reactors. Passage of the combined feed through the reaction zone produces an effluent stream comprising unconverted feed and product monoalkylated hydrocarbons. This effluent is normally cooled and passed to a stripping column in which substantially all $C_5$ and lighter hydrocarbons present in the effluent are concentrated into an overhead stream and removed from the process. An aromatics-rich stream is recovered as net stripper bottoms, which is referred to as the transalkylation effluent.

The transalkylation reaction can be effected in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner. The transalkylation zone normally operates at conditions including a temperature in the range of about 130° C. to about 540° C. The transalkylation zone is typically operated at moderately elevated pressures broadly ranging from about 100 kPa to about 10 MPa absolute. The transalkylation reaction can be effected over a wide range of space velocities. That is, volume of charge per volume of catalyst per hour; weight hourly space velocity (WHSV) generally is in the range of from about 0.1 to about 30 $hr^{-1}$. The catalyst is typically selected to have relatively high stability at a high activity level.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.). For isobutane alkylation, typically, the reactants are mixed in the presence of a strong acid catalyst, such as sulfuric acid or hydrofluoric acid. The alkylation reaction is carried out at mild temperatures, and is typically a two-phase reaction. Because the reaction is exothermic, cooling is needed. Depending on the catalyst used, normal refinery cooling water provides sufficient cooling. Alternatively, a chilled cooling medium can be provided to cool the reaction. The catalyst protonates the alkenes to produce reactive carbocations which alkylate the isobutane reactant, thus forming branched chain paraffins from isobutane. Aromatic alkylation is generally now conducted with solid acid catalysts including zeolites or amorphous silica-aluminas.

The alkylation reaction zone is maintained at a pressure sufficient to maintain the reactants in liquid phase. For a hydrofluoric acid catalyst, a general range of operating pressures is from about 200 to about 7,100 kPa absolute. The temperature range covered by this set of conditions is from about −20° C. to about 200° C. For at least alkylation of aromatic compounds, the temperature range is about from 100° C. to 200° C. at the pressure range of about 200 to about 7,100 kPa.

Oxidation involves the oxidation of hydrocarbons to oxygen-containing compounds, such as aldehydes. The hydrocarbons include alkanes, alkenes, typically with carbon numbers from 2 to 15, and alkyl aromatics, linear, branched, and cyclic alkanes and alkenes can be used. Oxygenates that are not fully oxidized to ketones or carboxylic acids can also be subjected to oxidation processes, as well as sulfur compounds that contain —S—H moieties, thiophene rings, and sulfone groups. The process is carried out by placing an oxidation catalyst in a reaction zone and contacting the feed stream which contains the desired hydrocarbons with the catalyst in the presence of oxygen. The type of reactor which can be used is any type well known in the art such as fixed-bed, moving-bed, multi-tube, CSTR, fluidized bed, etc. The feed stream can be flowed over the catalyst bed either up-flow or down-flow in the liquid, vapor, or mixed phase. In the case of a fluidized-bed, the feed stream can be flowed co-current or counter-current. In a CSTR the feed stream can be continuously added or added batch-wise. The feed stream contains the desired oxidizable species along with oxygen. Oxygen can be introduced either as pure oxygen or as air, or as liquid phase oxidants including hydrogen peroxide, organic peroxides, or peroxy-acids. The molar ratio of oxygen ($O_2$) to alkane can range from about 5:1 to about 1:10. In addition to oxygen and alkane or alkene, the feed stream can also contain a diluent gas selected form nitrogen, neon, argon, helium, carbon dioxide, steam or mixtures thereof. As stated, the oxygen can be added as air which could also provide a diluent. The molar ratio of diluent gas to oxygen ranges from greater than zero to about 10:1. The catalyst and feed stream are reacted at oxidation conditions which include a temperature of about 300° C. to about 600° C., a pressure of about 101 kPa to about 5,066 kPa and a space velocity of about 100 to about 100,000 $hr^{-1}$.

Hydrogenation involves the addition of hydrogen to hydrogenatable hydrocarbon compounds. Alternatively hydrogen can be provided in a hydrogen-containing compound with ready available hydrogen, such as tetralin, alcohols, hydrogenated naphthalenes, and others via a transfer hydrogenation process with or without a catalyst. The hydrogenatable hydrocarbon compounds are introduced into a hydrogenation zone and contacted with a hydrogen-rich gaseous phase and a hydrogenation catalyst in order to hydrogenate at least a portion of the hydrogenatable hydrocarbon compounds. The catalytic hydrogenation zone may contain a fixed, ebulated or fluidized catalyst bed. This reaction zone is typically at a pressure from about 689 kPag (100 psig) to about 13,790 kPag (2,000 psig) with a maximum catalyst bed temperature in the range of about 177° C. (350° F.) to about 454° C. (850° F.). The liquid hourly space velocity is typically in the range from about 0.2 $hr^{-1}$ to about 10 $hr^{-1}$ and hydrogen circulation rates from about 200 standard cubic feet per barrel (SCFB) (35.6 $m^3/m^3$) to about 10,000 SCFB (1778 $m^3/m^3$).

In some processes, all or a portion of the coal feed 10 and or coke stream 25 is mixed with oxygen 125 and steam 130 and reacted under heat and pressure in the gasification zone 20 to form syngas 135, which is a mixture of carbon monoxide and hydrogen. The syngas 135 can be further processed using the Fischer-Tropsch reaction to produce gasoline, diesel, or wax or using the water-gas shift reaction to produce more hydrogen.

Figure 2:
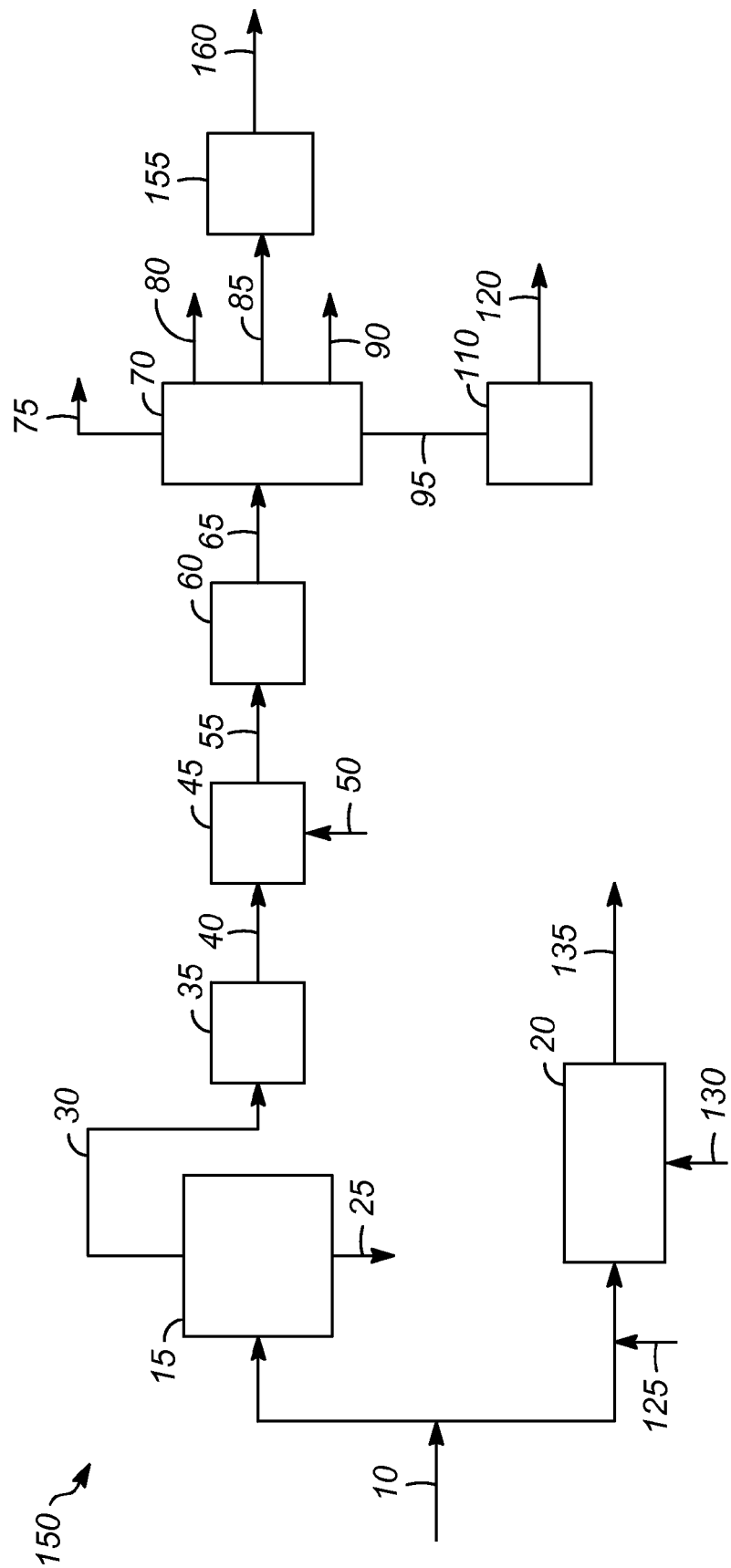
FIG. 2 illustrates another embodiment of the process of the present invention.

As shown in FIG. 2, another embodiment includes a process 150 for processing a coal tar feed stock to increase olefin production. In the process 150, zones that are substantially similar to the process 5 in FIG. 1 are numbered using identical reference numbers to aid understanding. The conversion product 65 is separated into its constituent streams 75, 80, 85, 90, 95, and at least the paraffin stream 85 is routed to a dehydrogenation zone 155. The paraffin stream 85 preferably includes low molecular weight paraffins, such as propane and butanes. In the dehydrogenation zone 155, the paraffins 85 are contacted with a dehydrogenation catalyst to dehydrogenate the paraffins. The catalyst preferably includes a platinum group metal component.

While exemplary embodiments have been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of processing a coal feed to produce aromatic hydrocarbon compounds, comprising:
    providing a coal tar stream;
    converting the coal tar stream by cracking said coal tar stream to a conversion product comprising at least olefins, paraffins, and aromatics;
    separating the olefins and C5$^-$ paraffins from the conversion product;
    contacting the separated olefins and the separated C5$^-$ paraffins with a catalyst comprising a gallium component and a crystalline aluminosilicate incorporated with a phosphorous containing alumina to dehydrogenize, oligomerize, and cyclize the olefins and the C5– paraffins, to form aromatic hydrocarbon compounds.

2. The method of claim 1, wherein converting the coal tar stream comprises catalytic cracking of the coal tar stream.

3. The method of claim 1, wherein converting the coal tar stream comprises thermal cracking of the coal tar stream.

4. The method of claim 1, wherein the conversion product further comprises non-aromatic $C_6^+$ hydrocarbons, and wherein said separating further comprises separating the non-aromatic $C_6^+$ hydrocarbons from the conversion product to produce a heavy hydrocarbon stream.

5. The method of claim 4, further comprising:
    reforming the heavy hydrocarbon stream by contacting the non-aromatic $C_6^+$ hydrocarbons with a catalytic reforming catalyst to produce aromatic hydrocarbon compounds.

6. The method of claim 5, wherein the catalytic reforming catalyst comprises platinum.

7. The method of claim 1, further comprising:
    hydrotreating the coal tar stream to remove one or more of sulfur, nitrogen, and oxygen from the coal tar stream to produce a hydrotreated coal tar stream before converting the coal tar stream.

* * * * *